United States Patent [19]

Burakoff et al.

[11] Patent Number: 5,115,098

[45] Date of Patent: May 19, 1992

[54] END-BLOCKED PEPTIDES INHIBITING BINDING CAPACITY OF GP120

[75] Inventors: Steven J. Burakoff, Newton; Stuart L. Schreiber, Boston, both of Mass.

[73] Assignees: President and Fellows of Harvard College, Cambridge; Dana-Farber Cancer Institute, Inc., Boston, both of Mass.

[21] Appl. No.: 486,522

[22] Filed: Feb. 28, 1990

[51] Int. Cl.$^5$ .............. A61K 37/02; C07K 5/06; C07K 5/08;
[52] U.S. Cl. ............... 530/331; 260/998.2; 514/18; 514/19; 530/345; 548/537
[58] Field of Search ......... 548/537, 538, 530, 540; 514/423, 19, 18; 226/998.2; 530/331, 335, 337, 345

[56] References Cited

U.S. PATENT DOCUMENTS

| | | | |
|---|---|---|---|
| 4,093,713 | 6/1978 | Lestany et al. | 548/357 |
| 4,416,871 | 11/1983 | Walter et al. | 514/19 |
| 4,456,594 | 6/1984 | Pfeiffa | 514/18 |
| 4,985,406 | 1/1991 | Charpentier et al. | 514/11 |

FOREIGN PATENT DOCUMENTS 56-018948 2/1981 Japan .

OTHER PUBLICATIONS

CA102:3717416, "Structural Study of benzyloxy Carbonyl Proalanyl tert-butyl ester", (1985).
"Potential anlinal agents: Carbobenzoxy di-Tripeptides", Nicolardes et al., vol. 11:76-79 (Jul. 1967).
Miller et al., "Anunal Activity of Carbobenzoxy di--Tripeptides on measles inus:Applied Miciobologic", 1489-1496.
CA87:53571q Theoretical Confanalysis on cyclo molyl phenylalanyl peptides, Ajo et al. (1977).
*Methoden Der Organischen Chemie (Houben-Weyl)*, Müller, Georg Thieme Verlag Stuttgart, 1974, p. 328.
Smith et al.; Blocking of HIV-1 Infectivity by a Soluble, Secreted Form of the CD4 Antigen; Science; 238:1704-1707; (Dec. 1987).
Fisher et al.; HIV infection is Blocked in vitro by Recombinant Soluble CD4; Nature; 331:76-78 (Jan. 1988).
Hussey et al.; A Soluble CD4 Protein Selectively Inhibits HIV Replication and Syncytium Formation; Nature; 331:78-81; (Jan. 1988).
Deen et al.; A Soluble Form of CD4 (T4) Protein Inhibite AIDS Virus Infection; Nature 331:82-84; (Jan. 1988).
Traunecker et al.; Soluble CD 4 Molecules Neutralize Human Immunodeficiency Virus Type 1; Nature; 331:84-86; (Jan. 1988).
Capon et al.; Designing CD4 Immunoadhesins for AIDS Therapy; Nature 337:525-531; (Feb. 1989).
Traunecker et al.; Highly Efficient Neutralization of HIV with Recombinant CD4-Immunoglobulin Molecules; Nature; 339:68-70; (May 1989).
Larder et al,: HIV with Reduced Sensitivity to Zidovudine (AZT) Isolated During Prolonged Therapy; Science; 243:1731-1734; (Mar. 1989).
Larder et al.; Multiple Mutations in HIV-1 Reverse Transcriptase Confer High-Level Resistance to Zidovudine (AZT) Science: 246:155-1158 (Dec. 1989).
Jameson et al.; Location and Chemical Synthesis of a Binding Site for HIV-1 on the CD 4 Protein; Science; 240:1355-1339; (Jun. 1988).
Lifson et al.; Synthetic CD4 Peptide Derivatives that Inhibit HIV Infection and Cytopathicity; Science; 241:712-716; (Aug. 1988).
Nara et al.; CD4 antigen-based Antireceptor Peptides Inhibit Infectivity of Human Immunodeficiency Virus in vitro at Multiple Stages of the Viral Life Cycle: Proc. Natl.; 86:7139-7143 (Sep. 1989).
Baba et al.; Mechanism of Inhibitory Effect of Dextran Sulfate and Heparin on Replication of Human Immuodeficiency Virus in vitro; Proc. Natl. Acad. Sci.; 85:6132-6136 (Aug. 1988).
Mitsuya et al.; Dextran Sulfate Suppression of Viruses in the HIV Family: Inhibition of Virion Binding to CD4+ Cells; Science; 240:646-649 (Apr. 1988).
Miller et al.; Antiviral Activity of Carbobenzoxy Di--and Tripeptides on Measles Virus; Applied Microbiology; 16:1489-1496; (Oct. 1968).
Burley et al.; Aromatic-Aromatic Interaction: A Mechanism of Protein Structure Stabilization; Science; 229:23-28; (Jul. 1985).
Nicolaides et al.; Potential Antiviral Agents, Carbobenzoxy Di-and Tripeptides Active against Measles and Herpes Viruses; II:74-79; (Jul. 1967).

*Primary Examiner*—Jeffrey E. Russel
*Attorney, Agent, or Firm*—Allegretti & Witcoff

[57] ABSTRACT

A C- and N-blocked prolyl-alanine compound having the structure

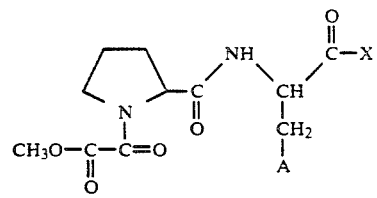

in which X is —OCH$_2$—B or

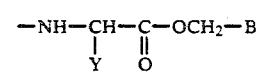

in which A and B are hydrogen or phenyl and Y is isobutyl inhibits binding capacity of GP120 and inhibits infection of cells by HIV-1.

4 Claims, No Drawings

END-BLOCKED PEPTIDES INHIBITING BINDING CAPACITY OF GP120

This invention was made with government support and the federal government has certain rights in the invention.

This invention relates to new ch cells were then pelleted, washed with 100 μl PBS and resuspended in fluorescein isothiocyanate conjugated goat anti-rabbit Ig (1:20:Tago) and incubated at 4° C. for 30 min. The cells were pelleted and washed as before, and resuspended in 100 μl of 25 μg/ml propidium iodide and transferred to tubes containing 400 μl PBS for flow cytometric analysis on an Epics V (Coulter) for RACScan (Becton-Dickenson). Cells were gated on propidium iodide to exclude dead cells. Green fluorescence was collected on the linear amplifier and the mean fluorescence calculated. Values were corrected by subtracting the mean fluorescence of cells treated with both antibodies but not exposed to gp120, which did not differ significantly from the intrinsic fluorescence of the cells, and was generally <15. 10 μg/ml is a subsaturating concentration for the baculovirus-produced gp120 used and the relation between fluorescence intensity and gp120 concentration approaches linearity.

The following inhibitor compounds were tested, referring to the general formula set forth above:
1. X is —OCH$_2$—B, A and B are phenyl, both amino acids are in the L-form;
2. X is —OCH$_2$—B, A is phenyl, B is hydrogen;
3. X is

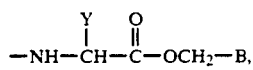

A and B are phenyl, and Y is isobutyl;
4. X is —OCH$_2$—B, A is hydrogen and B is phenyl;
5. X is —OCH$_2$—B, A and B are phenyl, both amino acids are in the D-form.

In each case the corrected mean fluorescence decreased as the concentration of the inhibitor increased from about 50 μM to 900 μM, showing increasing inhibition of binding to CD4 by the gp 120 which had been preincubated with an inhibitor compound.

EXAMPLE 2

100 μl solutions containing 20 μg/ml gp120 with and without 200 μg/ml of compound 5 above were incubated at 37° C. for 1 hour. 50 μl of each was diluted to 1 ml with PBS and then reconcentrated by ultrafiltration (20 min., 5.7 krpm in an SA-600 rotor; Dupont) in a Centricon-30 (molecular weight cutoff=30,000; Amicon). The Centricons were pretreated with 1% casein to reduce non-specific binding of gp120 to the device. The undiluted 50 μl aliquots, as well as a sample containing gp 120+10 μg/ml (the concentration of free inhibitor after ultrafiltration), were stored at 4° C. during ultrafiltration. These samples and the recovered retentates were then used to resuspend HSBCD4-M.23 and assayed as described in Example 1 above. Binding to the CD4 by the gp 120 pretreated as described above is inhibited to a similar extent both before and after dilution and ultrafiltration, as compared to untreated gp 120. Moreover, the extent of inhibition is greater than was obtained in Example 1 at the same concentration as the residual, showing that the inhibitor binds to and remains bound to the gp 120, and showing that the binding is not rapidly reversible, perhaps because the inhibitors are poorly soluble in water.

EXAMPLE 3

The physiologic ligands of CD4 are the Class II MHC proteins. This interaction is well known to promote conjugate formation in vitro between human CD4+ murine T cell hybridomas and Class II MHC− cells. Conjugate formation with Class II MHC− cells can also be observed with the HSBCD4-M.23 cells of Example 1. It has also been previously known that gp 120 inhibits conjugate formation. This inhibition is reversed by both compound 1 and compound 5, but not by compound 4 or compound 3. Inhibition of conjugates is observed either with preincubation of gp 120 and compound 1 or 5 or with simultaneous addition of components. These compounds have no effect on conjugate formation directly. Thus compounds 1 and 5 would not be expected to interfere with this aspect of T cell function. To the contrary they would reverse any inhibition due to gp 120.

Conjugate formational assays were performed using the CD4+ HSBCD4-M.23 and Class II MHC+ cell lines (Daudi). To evaluate the cell-cell conjugate formation the HSBCD4-M.23 cells were labeled with 0.5 μg/ml sulfofluorescein diacetate (Molecular Probes, Eugene, Oreg.) and Daudi cells were labeled with 40 ng/ml hydroethidine (Polysciences, Inc., Warrington, Pa.) by conventional methods. Cells at 1×10$^6$/ml were mixed at a 1:2 CD$^{4+}$/Class II MHC+ cell ratio and incubated at 37° C. for ≧60 min. in 30 μl or RPMI 1640, 10% fetal calf serum in 1.5 ml microcentrifuge tubes. Inhibitors, gp 120, and their mixtures were added simultaneously with the cells. Preincubation of gp 120-inhibitor mixtures was at 37° C. for 20-30 min. prior to addition. At the end of the incubation period samples were gently resuspended by repipetting 5 times through a tip having an internal diameter of 0.5 mm. To quantitate the percent of conjugates formed a 9 μl aliquot was placed on a glass slide and a 12 mm coverslip was placed over the sample and held in place with fingernail polish. Observations were made with a light microscope using a fluorescent lamp to locate the CD4$^{4+}$ fluorescein cells. A conjugate was defined as at least two cells of one color bound to at least one of the other. Blinded samples were run in duplicate and three or more counts of at least 100 fluorescein-labeled cells were done for each sample and scored as conjugates or non-conjugates. The percent of conjugates was calculated as the total number of conjugates divided by the total number of free CD4+ cells plus conjugates. Results are expressed as the mean value ±SEM of the six counts made for each group.

EXAMPLE 4

HIV-1 (strains HILViii$_B$ or MN) was derived from filtered (0.54μ) supernatants of H9 infected cells. Supernatants were incubated with compound 5 at 100 μm for 1 hour at 37° C. One ml specimens of the virus supernatant (with or without compound 5 at 100 μM) were incubated with 10$^6$ H9 cells at a multiplicity of infection of 10. Cells were washed three times and carried at 10$^5$ cells/ml in RPMI 1640 and 10% Fetal Calf Serum. Supernatants were analyzed at three day intervals up to a total of 15 days for production of p24 antigen by ELISA assay. No p24 antigen was found in the specimens containing compound 5, showing that compound 5 inhibits HIV infection of CD4+ T cells.

Similar results can be obtained with compounds in which one amino acid is in D-, the other in L-form.

The compounds, in a suitable pharmacologically acceptable non-toxic carrier can be administered to mammals such as man orally or by intravenous or intraarterial injection to inhibit infection by HIV.

What is claimed is:

1. A C- and N-blocked prolyl-alanine compound having the structure

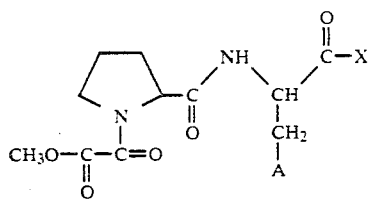

in which X is —OCH$_2$—B or

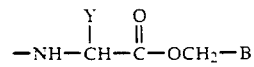

in which A and B are hydrogen or phenyl and Y is isobutyl.

2. A compound as claimed in claim 1 in which both the prolyl and the alanyl moieties are in the D-form.

3. A compound as claimed in claim 1 in which X is —OCH$_2$—B and A and B are phenyl.

4. A compound as claimed in claim 3 in which both the prolyl and the alanyl moieties are in the D-form.

* * * * *